US012636355B2

(12) United States Patent
Suarez et al.

(10) Patent No.: US 12,636,355 B2
(45) Date of Patent: May 26, 2026

(54) **TRANSMISSION-BLOCKING VACCINE AGAINST *BABESIA***

(71) Applicants: The United States of America, as represented by the Secretary of Agriculture, Washington, DC (US); Washington State University, Pullman, WA (US); James Cook University, Cairns (AU)

(72) Inventors: Carlos E Suarez, Pullman, WA (US); Jacob M Laughery, Pullman, WA (US); Reginaldo Gaspar Bastos, Pullman, WA (US); Marta Gomes Da Silva, Tübingen (DE); Heba Fathy Alzan, Harm (EG); Brian M Cooke, Cairns (AU); Vignesh A Rathinasamy, Cairns (AU)

(73) Assignees: The United States of America, as represented by the Secretary of Agriculture, Washington, DC (US); Washington State University, Pullman, WA (US); James Cook University, Cairns (AU)

( * ) Notice: Subject to any disclaimer, the term of this patent is extended or adjusted under 35 U.S.C. 154(b) by 608 days.

(21) Appl. No.: 17/953,025

(22) Filed: Sep. 26, 2022

(65) Prior Publication Data

US 2023/0190905 A1 Jun. 22, 2023

Related U.S. Application Data

(60) Provisional application No. 63/249,461, filed on Sep. 28, 2021.

(51) Int. Cl.
| | |
|---|---|
| *A61K 39/018* | (2006.01) |
| *A61P 33/02* | (2006.01) |
| *C07K 14/005* | (2006.01) |
| *A61K 39/00* | (2006.01) |

(52) U.S. Cl.
CPC ............ *A61K 39/018* (2013.01); *A61P 33/02* (2018.01); *C07K 14/005* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 7,722,879 | B2 | 5/2010 | Carcy et al. |
| 2011/0091526 | A1 | 4/2011 | Snell et al. |
| 2013/0323835 | A1 | 12/2013 | Mcdonald et al. |
| 2016/0158327 | A1 | 6/2016 | Suarez et al. |

FOREIGN PATENT DOCUMENTS

| | | |
|---|---|---|
| CN | 104845981 B | 6/2018 |

OTHER PUBLICATIONS

Hussein et al, PLoS Negl Trop Disclosed 11(10):e0005965, 2017. (Year: 2017).*
H.F. Alzan et al., 2021, Assessment of Babesia bovis 6cys A and 6cys B as components of transmission blocking vaccines for babesiosis, Parasit. Vectors. 14(1):210.
R.G. Bastos et al. 2009, "Silencing of a putative immunophilin gene in the cattle tick Rhipicephalus (Boophilus) microplus increases the infection rate of Babesia bovis in larval progeny," Parasit. Vectors. 2(1):57.
M. Florin-Christensen et al., 2014, "Vaccines against bovine babesiosis: where we are now and possible roads ahead," Parasitology, 141:1563-1592.
W. L. Goff et al., 1998, "Babesia bovis immunity. In vitro and in vivo evidence for IL-10 regulation of IFN-gamma and NOS," Ann. N. Y. Acad. Sci. 849: 161-180.
W.L. Goff et al., 1988, "Identification of Babesia bovis merozoite surface antigens by using immune bovine sera and monoclonal antibodies," Infect. Immun. 56(9): 2363-2368.
V. Rathinasamy et al., 2019, "Babesiosis Vaccines: Lessons Learned, Challenges Ahead, and Future Glimpses," Trends Parasitol. 35(8):622-635.
C.E. Suarez et al., 2019, "Unravelling the cellular and molecular pathogenesis of bovine babesiosis: is the sky the limit?" Int J Parasitol. 49(2):183-197.
C.E. Suarez et al., 2012, "Acute and persistent infection by a transfected Mo7 strain of Babesia bovis," Mol. Biochem. Parasitol. 185(1):52-57.
International Written Opinion on PCT/US2022/077072 mailed Jan. 27, 2023.
International Search Report on PCT/US2022/077072 dated Jan. 27, 2023.

* cited by examiner

*Primary Examiner* — Daniel E Kolker
*Assistant Examiner* — Cheom-Gil Cheong
(74) *Attorney, Agent, or Firm* — John Fado; Maria Restrepo-Hartwig

(57) ABSTRACT

The present invention relates to a *Babesia* antigen comprising at least a portion of a gametocyte HAPLESS2/GCS1 (HAP2) protein, vectors and cells expressing such antigen, compositions and kits comprising such antigens, and methods of using such antigens to interfere with the *Babesia* transmission by competent ticks.

8 Claims, 10 Drawing Sheets

Specification includes a Sequence Listing.

SEQUENCE LISTING

```
Sequence total quantity: 4
SEQ ID NO: 1           moltype = DNA  length = 1445
FEATURE                Location/Qualifiers
source                 1..1445
                       mol_type = other DNA
                       organism = synthetic construct
SEQUENCE: 1
catatggtaa taatatcaag tctaaggcaa tgtataaaca agggaactgg gaaagttacc   60
gaaagcgatt gccagtggcg tagccatacc aacgtggacg ttcgtggtgg cgagctgagc  120
accagctacg tgctgcgtaa gaaagataac ccgaacagcg gtctgtatat ccacattcag  180
accgcgatca ccaccctgac ctacaacctg gtgtatcaat tcgacgcgcc gtacatgtat  240
cgtgagcaca acggtgcgct ggaatacagc caggttgcgg gcatgtgcga cagctgcgat  300
aaaatcgaga ttaagaaatg caccctgccg gaggaagtgc cgccgaagct gaaggataag  360
tttgttaaca aaacctgctg catctgcggc aagaacgtgc cgagcaccgc ggttcgtcaa  420
aacctgaaat gcagcggttg gagcttcggc tttctgtaca ggacgcgcgt gagcctgagc  480
tgcctggaaa tcgttggccc gtggtacagc atttataagc cgcagtaccc gccggacatc  540
aaccgtcgta ttttcgtgga tgtttatagc tttgacggtg atgcgggcat cattccggac  600
gtgagcaaga aggttatca aaacagcaag ctgccggacg aaacccgtta cctgaaggaa  660
ccggtttata aagatggtca cctgaagttc accatgagca ccaacgcggg cgcggtgaaa  720
aacgaagacc tggatgttaa gtttaccatc attagccagc aatgggtgga cggcaacgcg  780
ccgatccgta tggataaata cgttgcggtt ccgacctggc cggacagcca cccggatgtt  840
cagggtagca gcctgcgttt cgagtgccag caagcggacc gtccgtatga atgccgtaag  900
ggccaagata acgagtgccg tatggaacgt tgcgcgctga acgtgcgtgt tattgaaccg  960
agcgcggtgg atgttaccgg tgcgacctgc gataaaattg gcgtgagcat gggtacctgg 1020
ggcgacgaga agcgtctgtg caaccagcac gaaggtacct gcatccagaa ccaactggcg 1080
tggtacttca aagaatttag cagcaccatg cgtctgccga agctgtatgg tagccaaccg 1140
atgatccgc acaaacgtat tagcggcagc gtgccggatg agaagaaaac cgttccgctg 1200
ccggcggaca aagaagcgat gaaggatgcg acctttagca gcaagccggc ggcggcggtt 1260
gcggcgaaaa ccccgaaggg tggcgcgaag aaaaagaaac agaaactgga cagcagcgag 1320
tgggaacaca aggatctgct gcacagcatc gcgtacaacg tgcgtcacgc ggacaccagc 1380
cgtatcgaga ttgacagctt cgatgcgacc atgaccctga tcattgcgga agcggttggt 1440
tttat                                                             1445

SEQ ID NO: 2           moltype = DNA  length = 21
FEATURE                Location/Qualifiers
source                 1..21
                       mol_type = other DNA
                       organism = synthetic construct
SEQUENCE: 2
gatgcgtttg cacatgctaa g                                             21

SEQ ID NO: 3           moltype = DNA  length = 20
FEATURE                Location/Qualifiers
source                 1..20
                       mol_type = other DNA
                       organism = synthetic construct
SEQUENCE: 3
cgggtacttc ggtgctctca                                               20

SEQ ID NO: 4           moltype = DNA  length = 33
FEATURE                Location/Qualifiers
source                 1..33
                       mol_type = other DNA
                       organism = synthetic construct
SEQUENCE: 4
cacgctcaag taggaaattt tgttaaacct gga                                33
```

TRANSMISSION-BLOCKING VACCINE AGAINST *BABESIA*

CROSS-REFERENCE TO RELATED APPLICATIONS

This application claims priority to U.S. Provisional Patent Application No. 63/249,461, filed Sep. 28, 2021. The content of this provisional patent application is hereby expressly incorporated by reference in its entirety.

FIELD OF THE INVENTION

The invention relates to compositions and methods for the control of *B. bovis* transmission by competent ticks.

SEQUENCE LISTING

The instant application contains a Sequence Listing XML required by 37 C.F.R. § 1.831(a) which has been submitted in XML file format via the USPTO patent electronic filing system, and is hereby incorporated by reference in its entirety. The XML file was created on 2022=09=26, is named Sequence_Listing-004921, and has 6 KB.

BACKGROUND OF THE INVENTION

Bovine babesiosis caused by the tick-borne apicomplexan parasite *Babesia bovis* is an economically important disease that threatens the cattle industry in the USA and worldwide. The disease results in high mortality and morbidity, and is characterized by anemia, fever, and sequestration of parasitized red blood cells (RBC) in blood capillaries, a feature shared with *Plasmodium falciparum*, that leads to the development of neurological symptoms.

Common strategies for the control of bovine babesiosis include tick vector suppression using acaricides, anti-*Babesia* drugs, and live attenuated vaccines. Eradication of tick vectors using acaricides is conceptually the most efficient method for preventing bovine babesiosis, but it is not practical, may have high toxicity, and may present with detrimental environmental effects. Furthermore, the continuous use of acaricides leads to the development of resistance by the ticks. In addition, currently available babesicidal drugs are costly, interfere with the development of herd immunity against the parasite, and may also generate resistance and toxicity in the cattle. Live vaccines based on blood stage attenuated parasites are relatively effective but have several limitations, including the risk of contamination with other pathogens, and reversion to virulence.

Thus, control of bovine babesiosis is currently inadequate, and new approaches are urgently needed.

SUMMARY OF THE INVENTION

Provided herein is an antigen comprising at least a portion of a *Babesia* gametocyte HAPLESS2/GCS1 (HAP2) protein, vectors expressing such antigen, compositions comprising such antigen, kits comprising such compositions, and methods for using such antigen to interfere with the transmission of *Babesia* by competent ticks.

In an embodiment, the invention relates to an antigen comprising at least a portion of a *Babesia* gametocyte HAPLESS2/GCS1 (HAP2) protein, and optionally at least one affinity tag. In some embodiments of the invention the HAP2 protein is from *B. bovis, B. bigemina, B. canis, B. caballi,* or *B. divergens*. In some embodiments of the invention, the antigen comprises at least a portion of a *Babesia* HAP2 protein and an affinity tag. In some embodiments of the invention, the antigen comprises at least a portion of a *B. bovis, B. bigemina, B. canis, B. caballi,* or *B. divergens* HAP2 protein. In some embodiments of the invention the at least a portion of a HAP2 protein in the *Babesia* antigen is encoded by at least a portion of the nucleotide sequence set forth in SEQ ID NO: 1. In some embodiments, the invention relates to a vector comprising a polynucleotide encoding a *Babesia* antigen comprising at least a portion of a HAP2 protein, and optionally an affinity tag. In some embodiments, the invention relates to a cell expressing a *B. bovis* antigen comprising at least a portion of a HAP2 protein, and optionally an affinity tag. In some embodiments of the invention the affinity tag is a polyhistidine tag.

In an embodiment, the invention relates to a composition encoding a *Babesia* antigen comprising at least a portion of a HAP2 protein and optionally an affinity tag, where the composition is a polynucleotide, a plasmid, or an expression vector. In an embodiment, the invention relates to a composition comprising a *Babesia* antigen comprising at least a portion of a HAP2 protein and optionally and optionally an affinity tag, where the composition is a host cell, a vaccine, or an immunogenic composition. In some embodiments of the invention, the at least a portion of a HAP2 protein is from *B. bovis, B. bigemina, B. canis, B. caballi,* or *B. divergens*

In an embodiment, the invention relates to a vaccine composition comprising a *Babesia* antigen comprising at least a portion of a HAP2 protein and optionally an affinity tag. In some embodiments of the invention, a vaccine composition comprising a *Babesia* antigen comprising at least a portion of a HAP2 protein comprises an affinity tag. In some embodiments of the invention, the vaccine composition comprising a *Babesia* antigen comprising at least a portion of a HAP2 protein further comprises at least one of an immunological adjuvant, a pharmaceutically acceptable carrier, a buffer, or a stabilizer.

In an embodiment, the invention relates to a method for interfering with *Babesia* transmission by competent ticks. The method comprises administering to cattle an effective amount of a vaccine composition comprising a *Babesia* antigen comprising at least a portion of a HAP2 protein, and optionally an affinity tag. Administration of an effective amount of a vaccine composition of the invention to cattle hampers transmission of *Babesia* by competent ticks that feed on the vaccinated cattle.

In an embodiment, the invention relates to a kit comprising a *Babesia* antigen comprising at least a portion of a HAP2 protein, and optionally an affinity tag. In some embodiments of the invention, the at least a portion of a HAP2 protein is from *B. bovis, B. bigemina, B. canis, B. caballi,* or *B. divergens*. In some embodiments of the invention, the affinity tag is a polyhistidine tag.

In an embodiment, the invention relates to a kit comprising a polynucleotide encoding a *Babesia* antigen comprising at least a portion of a HAP2 protein, and optionally an affinity tag. In some embodiments of the invention, the at least a portion of a HAP2 protein is from *B. bovis, B. bigemina, B. canis, B. caballi,* or *B. divergens*.

BRIEF DESCRIPTION OF THE DRAWINGS

FIG. 1A shows a picture of an SDS-PAGE gel. FIG. 1B shows a picture of a Western blot using mouse anti-6His antibody. In both images, the rHAP2 protein is indicated by an arrow. $M_1$ and $M_2$ are protein molecular weight marker standards whose size is indicated on the left.

FIG. 2A shows data for the individual calves. FIG. 2B shows mean and standard deviation (SD) of the data shown in FIG. 2A. The dotted line represents the cutoff value of the iELISA, calculated as the OD of non-infected cattle sera +3 SD. In both graphs the Y axis presents the absorbance at 450 nm, and the X axis presents the days after vaccination (0 to 94).

FIG. 3A presents the rectal temperature in ° F. measured for each calf at different days post-*B. bovis* challenge. FIG. 3B presents the mean calculated from the rectal temperature in ° C. measured for each calf at different days post-*B. bovis* challenge. FIG. 3C presents the Packed Cell Volume (PCV) measured for each calf at different days post challenge. FIG. 3D presents the mean calculated from the PCV measured for each calf at different days post challenge. The Y axis shows the temperature in FIG. 3A and FIG. 3B, and in the percent (%) PCV in FIG. 3C and FIG. 3D. The X axis on all graphs shows the days post challenge with virulent *B. bovis*.

FIG. 4A shows a graph of the *B. bovis* msa-1 gene copy number obtained for each of the calves vaccinated with rHAP2 in adjuvant (1646; 1647, 1649), the calves vaccinated with adjuvant alone (1650, 1652, 1653), the mean of the msa-1 gene copy number in calves vaccinated with rHAP2 in adjuvant (Vaccinated), and the mean of the msa-1 gene copy number in the calves vaccinated with adjuvant alone (Control). The Y Axis presents the Log square mean of the *B. bovis* msa-1 gene copy number, and the X Axis presents the animals. FIG. 4B shows the number of copies of *B. bovis* msa-1 gene obtained by qPCR on gDNA extracted from blood of infected calves. The Y axis presents the copies of *B. bovis* msa-1 gene per 10 µl of blood, and the X axis shows the days post-challenge with virulent *B. bovis*.

FIG. 5A shows the total number of engorged ticks recovered from calves vaccinated with rHAP2 in adjuvant (1646; 1647, 1649), calves vaccinated with adjuvant alone (1650, 1652, 1653), total number recovered from rHAP2-vaccinated animals (Vaccinated), and total number recovered from control animals (Control). FIG. 5B shows the mean and standard deviation of the number of engorged female *R. microplus* ticks recovered from rHAP-2-vaccinated animals and control animals. The Y axis presents the number of engorged ticks, and the X axis presents the animals tested.

FIG. 6A presents the rectal temperature in ° F. measured for each calf at different days post challenge. FIG. 6B presents the mean and standard deviation of the rectal temperature in ° C. measured for each calf at different days post challenge. FIG. 6C presents the Packed Cell Volume (PCV) for each calf at different days post challenge. FIG. 6D presents the percent (%) PCV mean and standard deviation at different days post challenge. Calves C99555, C99556, and C99557 received larvae derived from ticks that were acquisition-feeding on calves vaccinated with rHAP2, and calves C99559, C99561, and C99562 received larvae derived from ticks that were acquisition-feeding on control calves. The X axis on both graphs shows the days post tick infestation.

FIG. 7A presents the msa-1 gene number copies detected per 0.5 µg DNA. The X axis shows the calf numbers and the date in which the blood and gDNA samples were collected. FIG. 7B presents of the mean and standard deviation of the *B. bovis* msa-1 gene on DNA extracted from blood from calves receiving ticks derived from rHAP2-vaccinated calves or from control calves 10 days post-tick infestation. The Y axis represents the msa-1 gene number copies detected per 10 µl DNA. The X axis shows the calf numbers: 1=C99555, 2=C99556, 3=C99557, 4=C99559, 5=C99561, 6=C99562.

FIG. 8A presents the levels *B. bovis* RAP-1 antibodies detected before and after immunization, and the date in which the samples were collected. FIG. 8B presents the levels *B. bovis* RAP-1 antibodies detected in rHAP2-vaccinated calves prior to tick infestation and 30 days post-tick infestation. C37816 represents iELISA analysis performed on sera from a calf experimentally infected with *B. bovis*. BABB75 represents an iELISA positive control for RAP-1. In both graphs the Y axis represents OD at 435 nm, and the X axis shows the origin of the samples.

BRIEF DESCRIPTION OF THE SEQUENCE LISTING

Figure 1A:
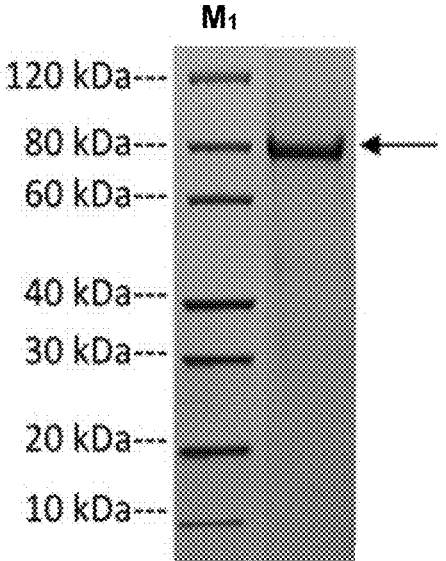
FIG. 1A and FIG. 1B depict images of an SDS-PAGE gel and a Western blot of Ni-column-purified *B. bovis* rHAP2 protein confirming its molecular weight and purity.

The nucleotide sequences disclosed in the specification are listed in Table 1, below.

| Sequence Identifier | Type | Description |
|---|---|---|
| SEQ ID NO: 1 | DNA | Codon-optimized sequence encoding HAP2 |
| SEQ ID NO: 2 | DNA | GATGCGTTTGCACATGCTAAG |
| SEQ ID NO: 3 | DNA | CGGGTACTTCGGTGCTCTCA |
| SEQ ID NO: 4 | DNA | CACGCTCAAGTAGGAAATTTT GTTAAACCTGGA |

DETAILED DESCRIPTION

Provided herein is a *Babesia* antigen comprising at least a portion of a gametocyte HAPLESS2/GCS1 (HAP2) protein and optionally at least one affinity tag, vectors expressing such antigen, compositions and kits comprising such antigen, and methods of using such compositions to interfere with the transmission of *B. bovis* by competent ticks.

The apicomplexan *Babesia bovis* is responsible for bovine babesiosis, a poorly controlled tick-borne disease of global impact. The lifecycle of *B. bovis* is complex, including sexual reproduction in the midgut of its biological tick vectors, mainly *Rhipicephalus microplus* and *R. annulatus*, and asexual reproduction inside cattle erythrocytes. The mechanism of sexual reproduction of *B. bovis* has not been fully elucidated, but previous studies identified key proteins of the process, including the gene expression regulators AP2 proteins, the widely conserved 6 Cys and CCp proteins, and the HAPLESS 2 (HAP2) protein.

A possible alternative strategy is the use of subunit vaccines that may prevent acute babesiosis. Subunit vaccines against bovine babesiosis are recognized as an important need but remain unavailable despite the efforts of numerous researchers for many years. Subunit vaccines can be composed of a single or a combination of several protective antigens, selected among those expressed in blood stages of *B. bovis*. Currently, there is not a single effective subunit vaccine available in the market against any medically/veterinary significant apicomplexan pathogen. This is likely due in part to the complexity of such agents, our incomplete knowledge of the nature of protective immune responses, and the ability of these agents to escape the immune system and produce acute and persistent infections.

To date many of these antigens have been explored and tested as candidate subunit vaccines, but such vaccines remain unavailable (Florin-Christensen M. et al., "Schnittger L. 2014, "Vaccines against bovine babesiosis: where we are now and possible roads ahead," Parasitology, 28:1-30; Suarez C E et al., "Unravelling the cellular and molecular pathogenesis of bovine babesiosis: is the sky the limit?" Int J Parasitol. 49(2):183-197; Rathinasamy V. et al., 2019, "Babesiosis Vaccines: Lessons Learned, Challenges Ahead, and Future Glimpses," Trends Parasitol. 35(8):622-635). The first *B. bovis* transmission-blocking vaccine trial performed in cattle was based on the 6-cys A and 6-Cys B proteins. Vaccination of cattle with these two proteins failed in eliciting protective immune responses against transmission of the parasite (Alzan H F et al., 2021, Assessment of *Babesia bovis* 6cys A and 6cys B as components of transmission blocking vaccines for babesiosis," Parasit. Vectors. 14(1):210).

HAP2 is a conserved membrane protein, homologous to class II viral fusogen, expressed by male gametocytes, and essential for gamete fusion in a diverse array of eukaryotes, including plants, protozoan, and other metazoans. The single copy hap2 gene of *B. bovis* has been shown to be differentially expressed by parasites in the tick midgut, and on the surface of in vitro-induced sexual stages of the parasite. Consistently, the hap2 gene has also been found expressed in midgut stages of the highly related *B. bigemina*. Expression of HAP2 has been recognized as critical for the fertilization of the *Babesia*-related parasites *Plasmodium*. Importantly, both *Babesia* and *Plasmodium* share the occurrence of sexual reproduction in the midgut of *Rhipicephalus* ticks and *Anopheles* mosquitoes, respectively. Furthermore, antibodies against recombinant HAP2 of *P. falciparum* can induce transmission-blocking antibodies, and specific antibodies against HAP2 of *B. bigemina* are able to block zygote formation. In addition, *B. bovis* hap2-KO parasites were not able to develop sexual stages in an in vitro sexual stage induction-system, demonstrating the essential role played by HAP2 in fertilization. Experiments performed with *P. vivax* anti-recombinant HAP2 antibodies using an *Anopheles dirus* membrane feeding system demonstrated the ability of the antibodies to interfere with sexual reproduction of the parasite and to reduce infection of *P. vivax* in feeding mosquitos. Collectively, these results provide strong rationale supporting HAP2 as a candidate for the development of transmission blocking vaccines (TBV) against arthropod-transmitted *Babesia* and *Plasmodium* apicomplexan parasites. However, all these published studies were performed in vitro models of tick feeding or sexual stage induction, and no vaccine trials of HAP2 involving natural hosts and transmission-acquisition models have been reported to date.

Figure 1B:
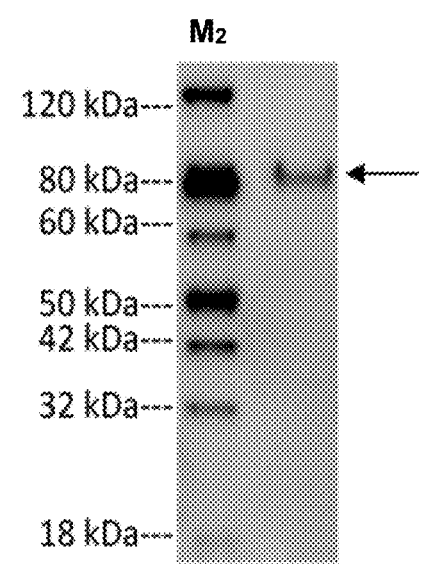

The inventors surprisingly found that vaccinating calves with an *B. bovis* antigen comprising at least a portion of a gametocyte HAPLESS2/GCS1 (HAP2) protein interfered with *B. bovis* transmission by competent ticks. The inventors prepared a recombinant HAP2 protein (rHAP2) containing a histidine tag to assist in purification. As seen in FIG. 1A, the protein purified through a Ni column ran at the expected molecular weight. Similarly, the Western blot on FIG. 1B shows that the mouse anti-6His antibody produced a single band on a Western Blot containing the Ni-column purified protein.

Figure 2A:
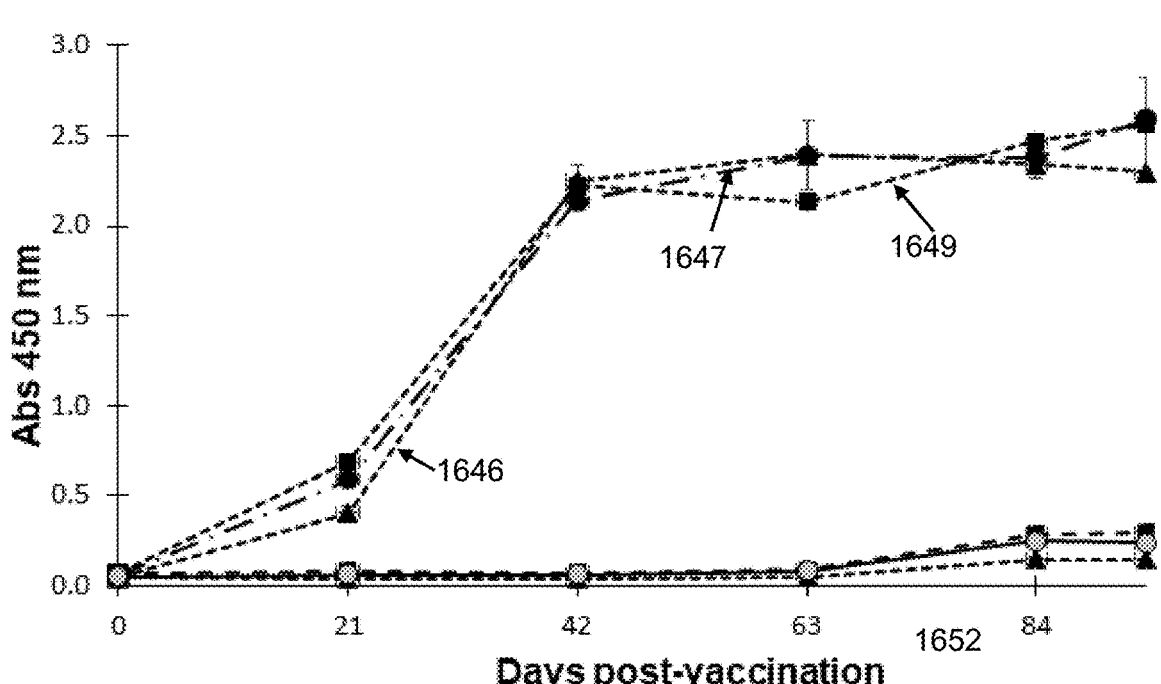
FIG. 2A and FIG. 2B depict graphs of the rHAP2 antibodies detected on calves vaccinated with rHAP2 in adjuvant (1646; 1647, 1649), and calves vaccinated with adjuvant alone (controls: 1650, 1652, 1653).
Figure 2B:
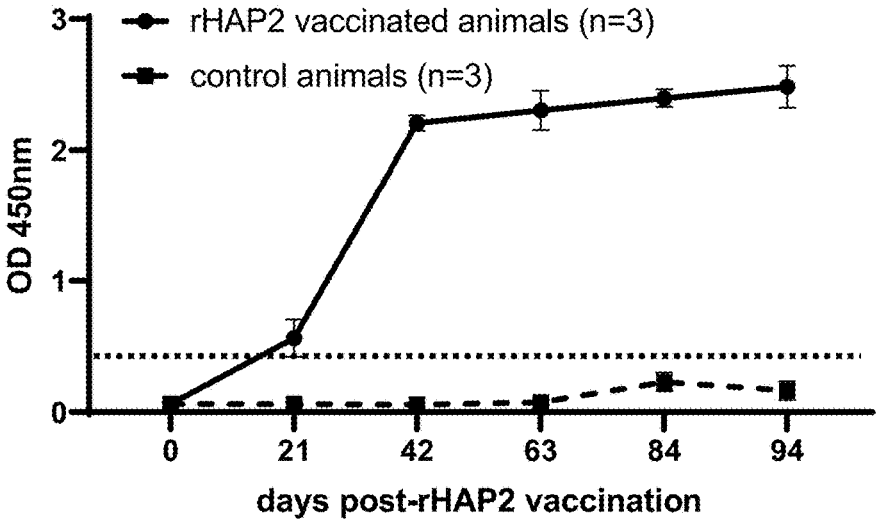

As can be seen in FIG. 2A and FIG. 2B, calves vaccinated with the *B. bovis* antigen (n=3) developed significant levels of antibodies against HAP2. Calves vaccinated with adjuvant alone, control animals (n=3), did not develop detectable levels of antibodies against HAP2. Vaccinated and control animals were then infested with *Rhipicephalus microplus* larvae, and later infected with *B. bovis* by needle infection. As can be seen in FIG. 3A to FIG. 3D, all animals developed similar typical symptoms of acute babesiosis, suggesting that vaccination with the *B. bovis* antigen of the invention does not protect against acute *B. bovis* infection. Collected engorged female ticks fed on these acutely-infected calves were incubated for larval recovery. Transmission-feeding was conducted using pools of larvae derived from ticks fed on either *B. bovis* antigen-vaccinated calves or control calves. Three calves exposed to larvae derived from control donors developed acute signs of babesiosis within 11 days. None of the three calves challenged with larvae from ticks fed on *B. bovis* antigen-vaccinated animals developed signs of babesiosis even after 11 days. *B. bovis* DNA and antibodies against *B. bovis* were found in all diseased control animals, but none was detected in calves exposed to larvae derived from *B. bovis* antigen-vaccinated animals. These results are consistent with lack of *B. bovis* transmission in *B. bovis* antigen-vaccinated animals.

Figure 4A:
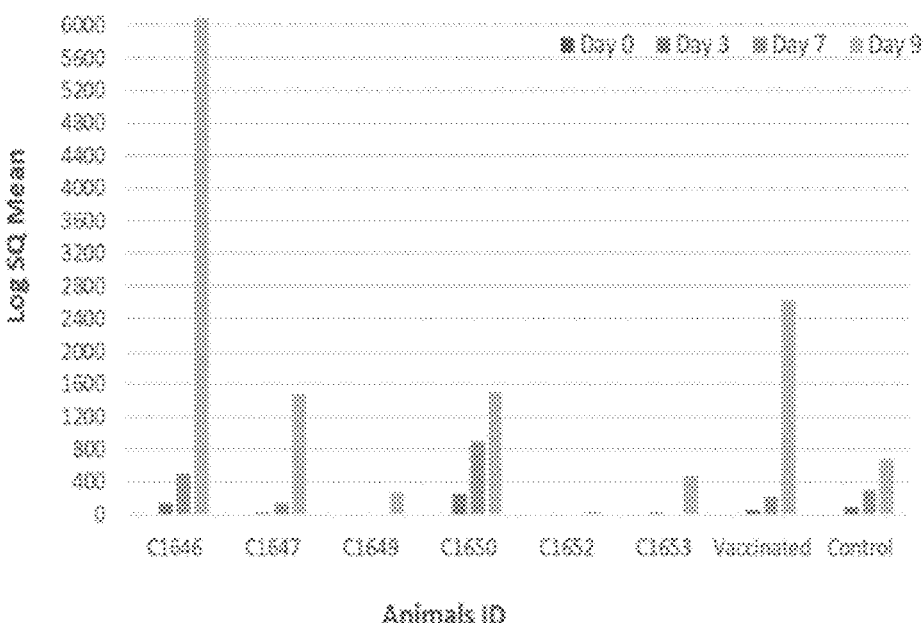
FIG. 4A and FIG. 4B depict graphs of the *B. bovis* msa-1 gene copy number obtained by qPCR on gDNA extracted from blood of infected calves at days 0, 3, 7- and 9-days post-infection.
Figure 4B:
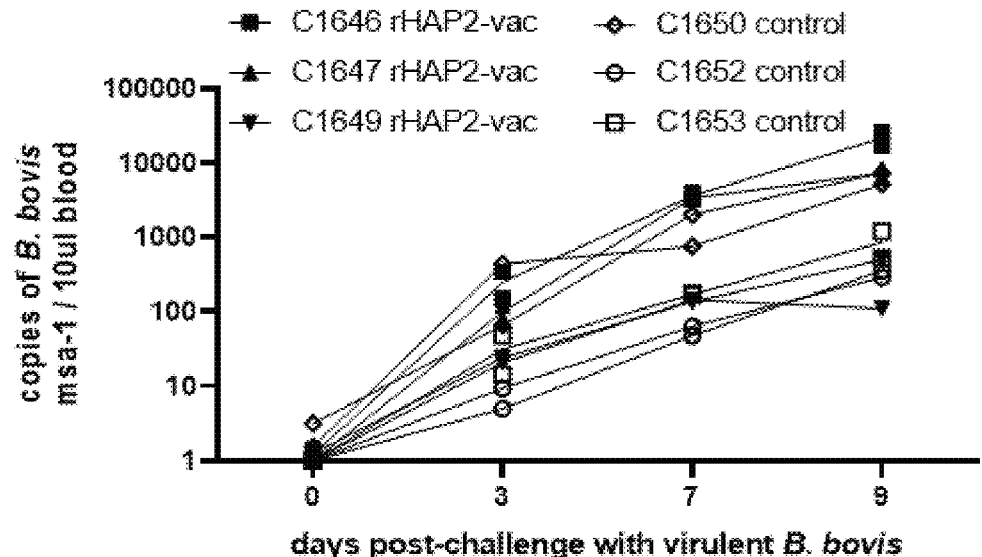

The *B. bovis* msa-1 gene copy number obtained by qPCR on gDNA extracted from blood of infected calves is shown in FIG. 4A and FIG. 4B. In FIG. 4A the results are presented as copies of *B. bovis* msa-1 per 0.5 µg of gDNA, and in FIG. 4B the results are presented as copies of *B. bovis* msa-1 per 10 µl of blood. As seen in these figures, the levels of msa-1 gene DNA detected among the infected calves were highly variable among all the time points tested. However, no statistical differences were found in the qPCR data on days 0 (P=0.64), 3 (P=0.69,) 7 (P=0.81) and 9 (P=0.38) post challenge, among grouped rHAP2 vaccinated (C1646, C1647 and C1649) and control adjuvant inoculated (C1650, C1652 and C1653) calves.

Figure 5A:
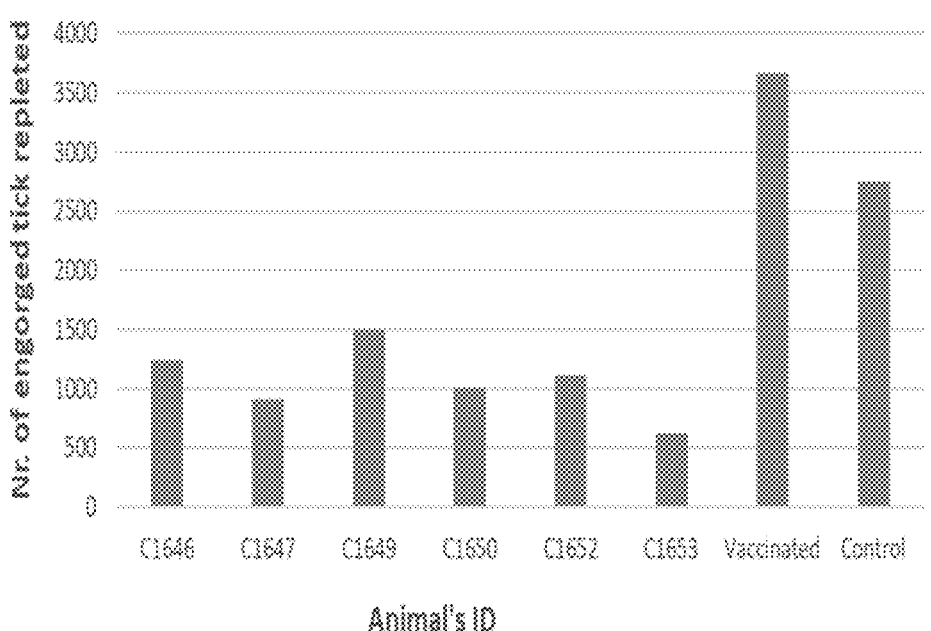
FIG. 5A and FIG. 5B depict graphs of the number of engorged adult female *R. microplus* ticks recovered from the tested experimental animals.
Figure 5B:
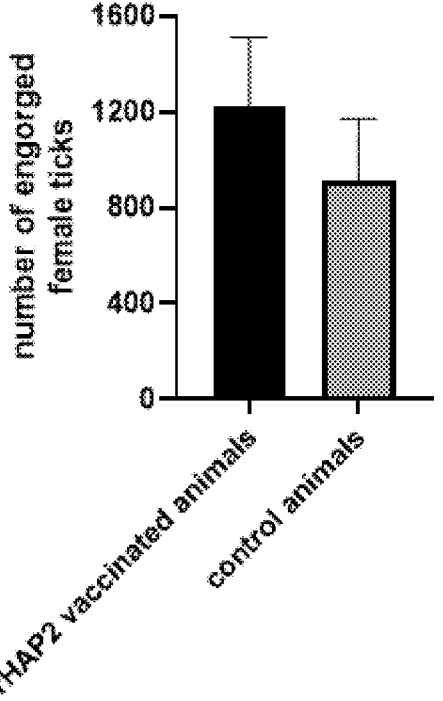

Engorged female ticks were collected daily from days 6 to 10 of feeding, coinciding with the peak of *B. bovis* parasitemia. The total number of replete ticks recovered per animal is shown in FIG. 5A and FIG. 5B. Interestingly, the total number of replete female ticks recovered from vaccinated calves (about 3,600) was significantly larger than the total number of replete female ticks recovered from control animals (about 2,600). The total weight of ticks from the vaccinated animals was 207.9 grams, while total weight of ticks from the control animals was 184.4 grams (n=48). Despite this trend, no statistical difference was found between weights of the vaccinated and the control groups (P=0.06). Interestingly, the weight of eggs from ticks fed on vaccinated and control groups was statistically different (P=0.023). Total eggs weight over the 5 days was 57.9 grams on vaccinated animals and 49.4 grams on control animals (n=48).

Figure 6A:
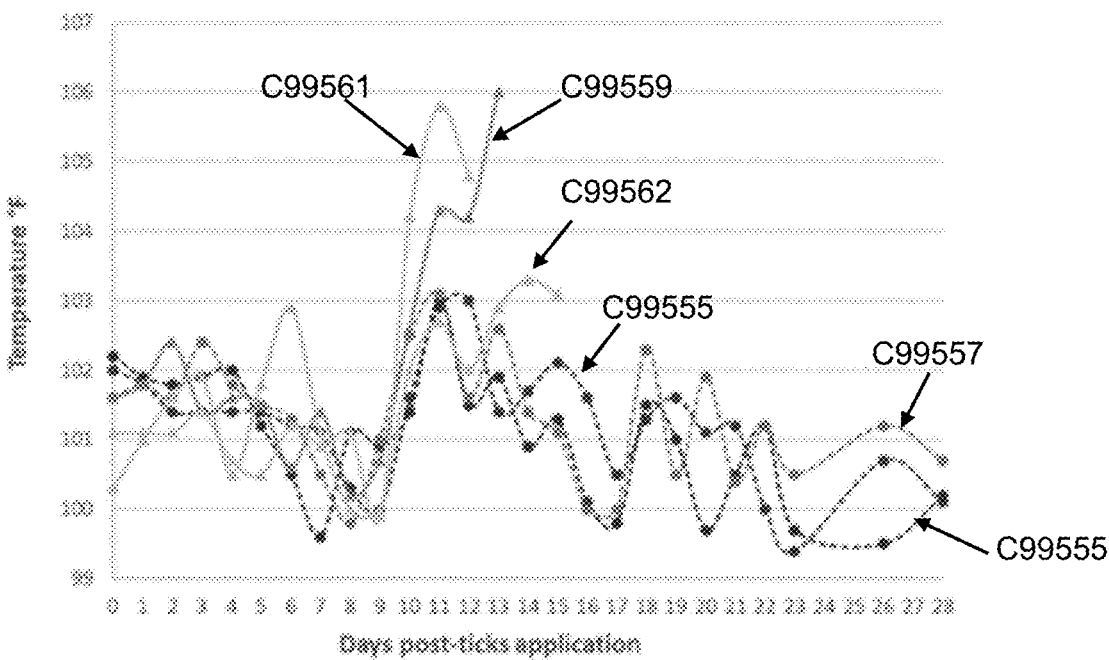
FIG. 6A to FIG. 6D depict graphs of the clinical parameters on transmission feeding calves challenged with tick larvae derived from rHAP2-vaccinated (1646; 1647, 1649) or control calves (1650, 1652, 1653) infected with *B. bovis* S74-T3Bo.
Figure 6B:
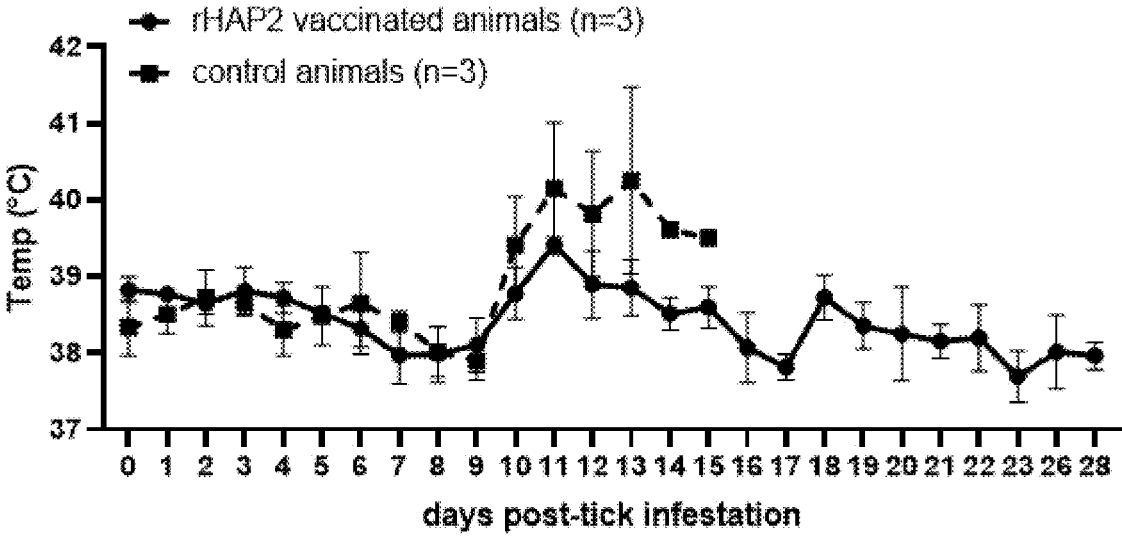
Figure 6C:
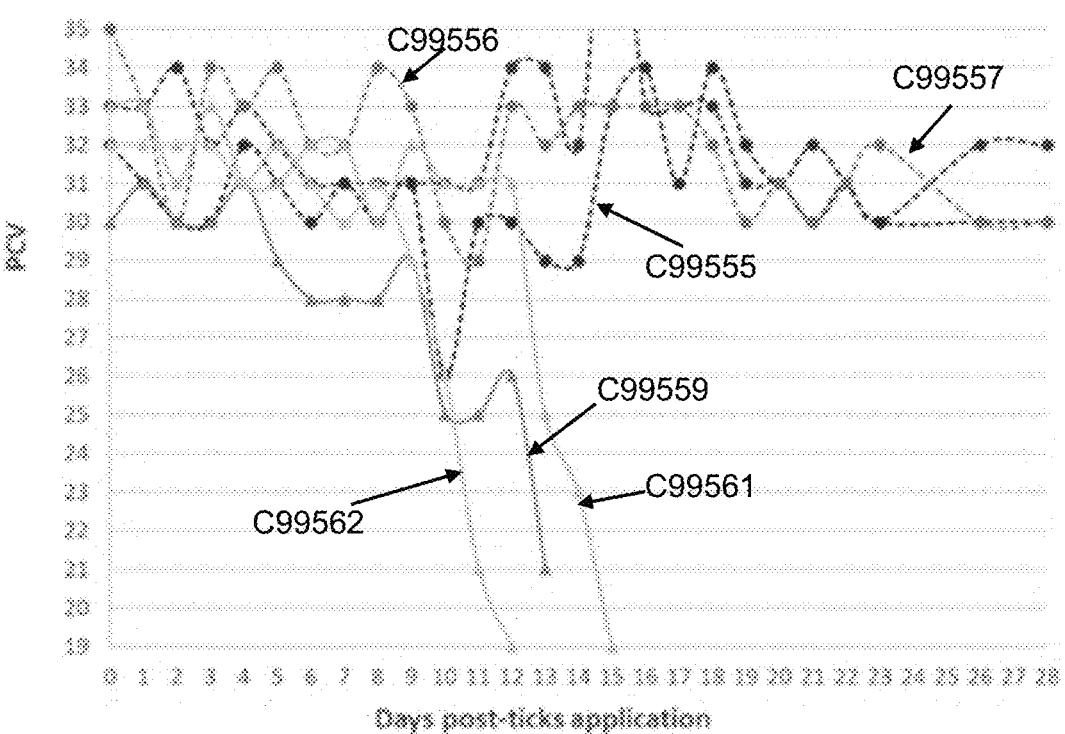
Figure 6D:
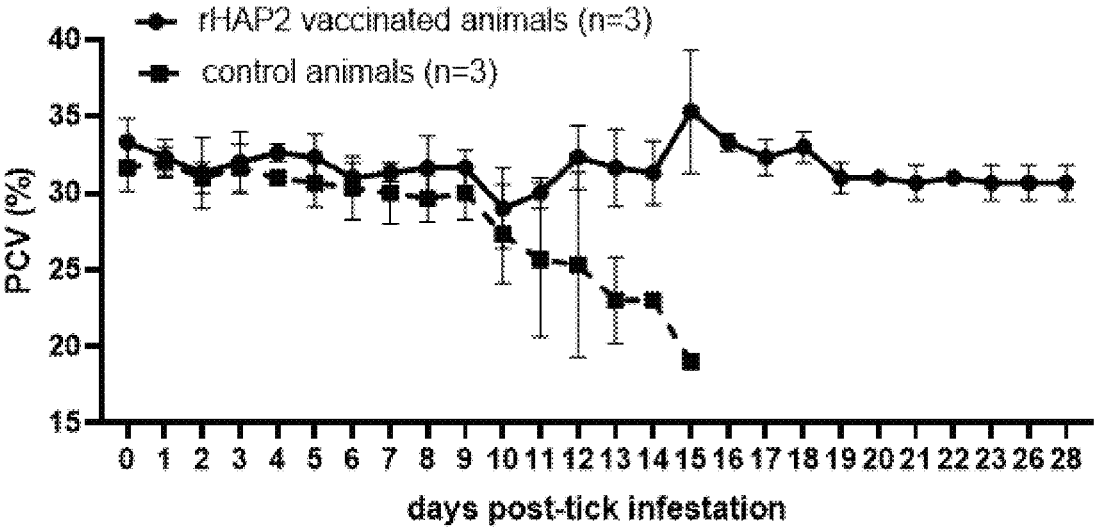
Figure 7A:
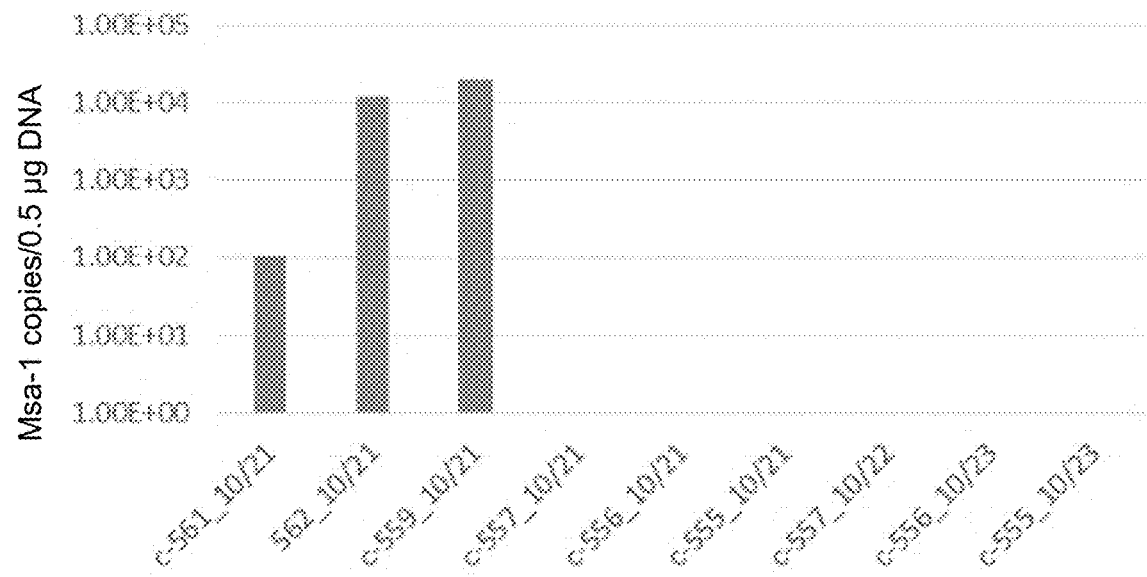
FIG. 7A and FIG. 7B depict graphs of the amount of *B. bovis* DNA detected by quantitative PCR (qPCR) based on the *B. bovis* msa-1 gene on DNA extracted from blood from calves receiving ticks derived from rHAP2-vaccinated calves (C99555, C99556, C99557), or from control calves (C99559, C99561, C99562).
Figure 7B:
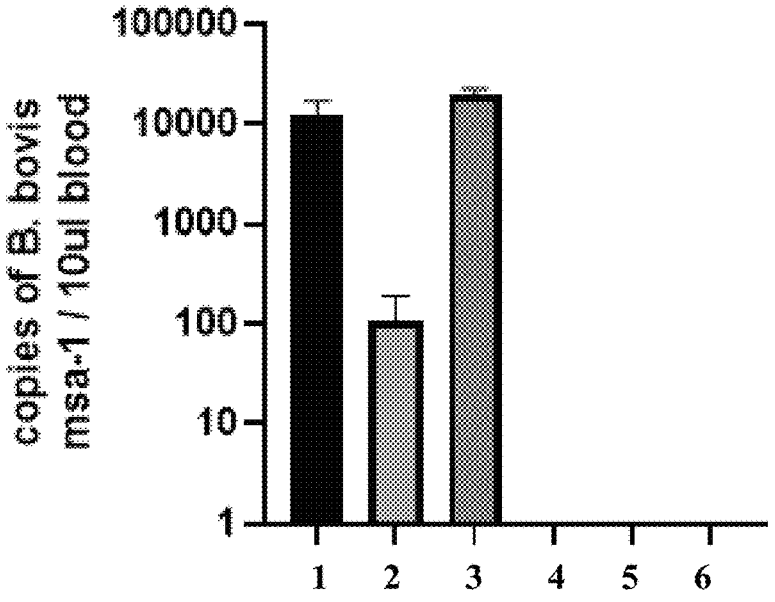
Figure 8A:
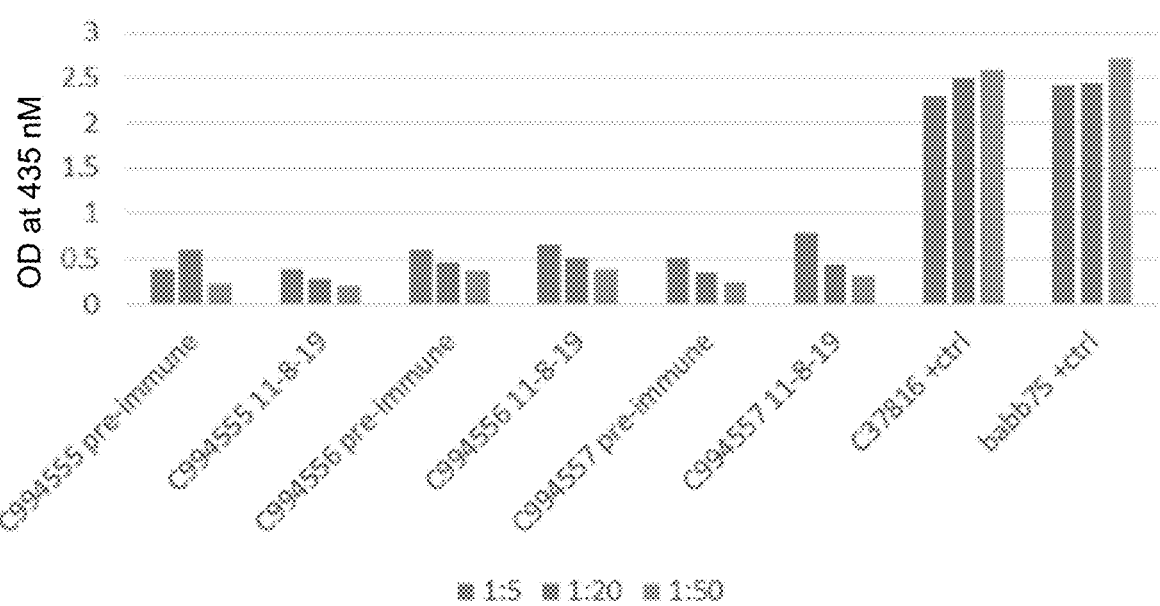
FIG. 8A and FIG. 8B depict graphs of the levels *B. bovis* RAP-1 antibodies detected by iELISA on sera from calves receiving ticks derived from rHAP2-vaccinated calves, or from control calves.
Figure 8B:
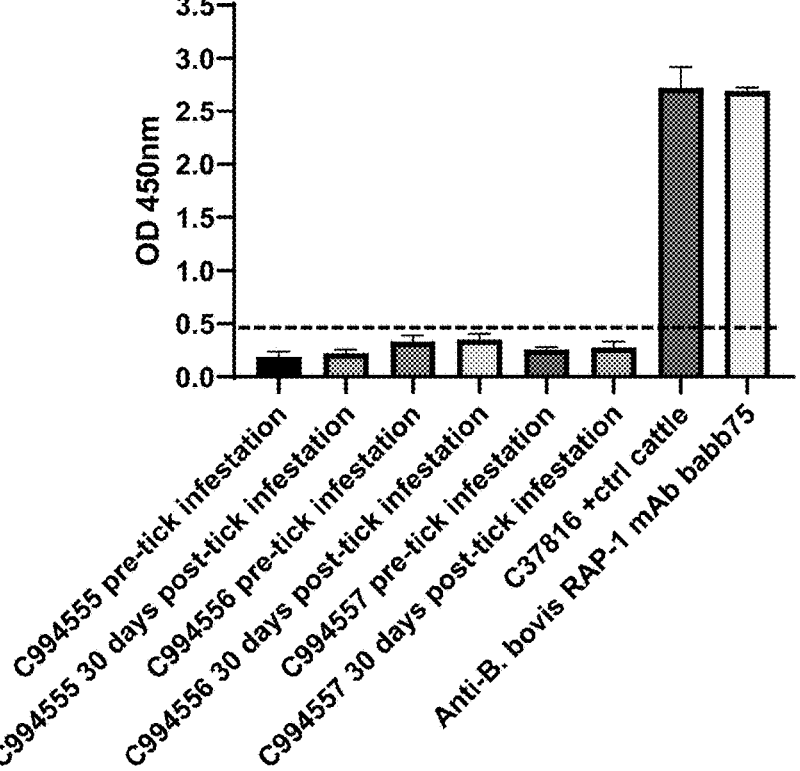

As seen in FIG. 6A and FIG. 6B, none of the calves infested with larvae from HAP2-vaccinated animals displayed detectable fever, and as seen in FIG. 6C and FIG. 6D, no significant decrease in PCV was detected in any of the rHAP3-vaccinated animals. In contrast, the three calves in the control group showed fever (higher than 38.8° C.), a significant drop in PCVs (30%), and typical clinical symptoms of acute babesiosis, such as prostration, anorexia, and increased respiratory lethargy. All experimental calves were also analyzed for the presence of parasite DNA by qPCR, and for the presence of immune humoral responses against *B. bovis* by iELISA. As seen in FIG. 7A and FIG. 7B, the presence of *B. bovis* DNA was detected in all control animals, but not in the three calves that received tick larvae from the HAP2-vaccinated animals. In addition, as seen in FIG. 8A and FIG. 8B, none of the three asymptomatic animals developed antibodies against *B. bovis* until the end of the experiment, 18 days after exposure to the ticks. The lack of antibodies in these three animals was also confirmed by Western blot analysis. Control calves were humanely euthanized at day 13 after larvae infestation due to the severity of acute babesiosis.

Affinity tags are peptide-encoding polynucleotides appended to proteins to assist in their detection, characterization, and/or purification. Examples of affinity tags are nHis, nArg tag, GST, FLAG tag, SBP, Strep tag, Strep II tag, twin Strep tag, CBP, CBD, MBP, CBP, and HAT. Polyhistidine tag (nHis), is a poly-histidine polypeptide that can be located at the N-terminus or C-end of a recombinant protein. A polyhistidine tag does not affect, the structure and/or function of the purified protein, thus, it is one of the most frequently used affinity tags. Recombinant His-tagged proteins are purified using metal ion affinity chromatography, nickel, cobalt, and copper are the most common metals used. Polyarginine tag (Poly-Arg or nArg tag) typically consists of five or six consecutive arginines at the C-terminal end of a recombinant protein. A polyarginine tag causes the recombinant protein to have a positively charged end with affinity for a negatively charged sorbent, which may affect the tertiary structure of the protein and/or the protein's properties. Recombinant Arg-tagged proteins are purified using a cation exchange resin. Glutathione-S-transferase (GST) is a 211 amino acid polypeptide attached to either the N-terminus or C-end of a protein. The GST tag increases solubility of the desired protein. Recombinant GST-tagged proteins are purified using a reduced glutathione resin. FLAG tag is an eight amino acid peptide added at either the N-terminus or C-end of a protein. Due to its small size, the FLAG tag has very little interfering effect on protein folding. But FLAG tag is eluted using low pH, which may irreversibly affect the recombinant protein properties.

Streptavidin-binding peptide or Streptavidin-binding protein (SBP) is a 38 amino acid peptide that may be added at the N-terminus or the C-terminus of a protein. Recombinant proteins containing a SBP-tag bind to streptavidin. The streptavidin-binding tag (Strep-tag) is a nine amino acid tag that is added to the C-end of a protein. Strep-tag displays intrinsic binding activity towards streptavidin, and can be efficiently eluted using free biotin. STREP-TAG also called modified streptavidin-binding tag, is a small affinity peptide that may be added to the C-terminus of N-end of a protein. STREP-TAG II is inert, largely resistant to cellular proteases, and can be used with mild detergents. Twin-Strep tag consists of two STREP-TAG II moieties connected by a short linker that may be added at the N-terminus or the C-end of a protein.

Calmodulin binding peptide, or Calmodulin binding protein (CBP) is a C-terminal 26 amino acid fragment derived from muscle myosin light-chain kinase. This small fragment may be added at the N-terminus or the C-end of a protein, and displays a strong affinity for calmodulin. The chitin-binding tag or chitin-binding domain is a 51 amino acid fragment from *Bacillus circulans* and may be added at the N-terminus, the C-end, or both termini of a protein. The recombinant protein binds with the chitin immobilized on Sepharose under physiological conditions. Maltose-binding protein (MBP) is an *E. coli* periplasmic protein that can be expressed at very high levels. The MBP tag may be added at either the C-terminus or the N-end of a protein. Recombinant proteins tagged with MBP are purified using affinity chromatography on amylose. The fungal cellulose-binding domains (CBDs) and can be joined to either the C-terminus or N-end of the recombinant protein. Purification of CBD-tagged proteins is done using a cellulose column. Natural histidine affinity tag epitope (HAT) is a naturally-occurring sequence of non-adjacent histidine residues that has a lower overall charge than tags with consecutive His residues. HAT-protein fusions exhibit solubility that more closely resembles that of wild-type proteins, while still possessing strong affinity for immobilized metal ions.

In an embodiment, the antigen of the invention comprises a *Babesia* gametocyte HAPLESS2/GCS1 (HAP2) protein. In some embodiments of the invention, the HAP2 protein is from *B. bovis, B. bigemina, B. canis, B. caballi,* or *B. divergens*. In some embodiments, the *Babesia* antigen of the invention may optionally comprise at least one affinity tag. In some embodiments of the invention, the at least one affinity tag present in the *Babesia* antigen may be a polyhistidine tag. In some embodiments of the invention, the at least a portion of a HAP2 protein is encoded by at least a portion of the polynucleotide having the sequence set forth in SEQ ID NO: 1.

Recombinant polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle. Accordingly, the invention provides methods of producing a polypeptide of the invention, the method comprising inserting a polynucleotide encoding at least a portion of a HAP2 protein into an expression vector, and transforming the vector into a host cell; and isolating the polypeptide from the host cell.

In an embodiment, the invention relates to a vector comprising a polynucleotide encoding the *Babesia* antigen of the invention. A vector is a DNA molecule used as a vehicle to artificially carry foreign genetic material into another cell, where it can be replicated and/or expressed (e.g., plasmid, cosmid, Lambda phages). The four major types of vectors are plasmids, viral vectors, cosmids, and artificial chromosomes. Of these, the most commonly used vectors are plasmids. Common to all engineered vectors have an origin of replication, a multicloning site, and a selectable marker.

Those skilled in the field of molecular biology will understand that any of a wide variety of expression systems may be used to provide the *Babesia* antigen of the invention. The precise host cell used is not critical to the invention. A *Babesia* antigen of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources. The method of transformation or transfection and the choice of expression vehicle will depend on the host system selected.

In an embodiment, the invention relates to a composition encoding the *Babesia* antigen of the invention, wherein the composition is a polynucleotide, a plasmid, or an expression vector. In an embodiment, the invention relates to a composition comprising the *Babesia* antigen of the invention, where the composition is a host cell, a vaccine, or an immunogenic composition.

A vaccine or immunogenic composition provided herein can be in the form of a recombinant HAP2 or fragment thereof involved in evoking an immune response to *Babesia*. In some embodiments, the vaccine or immunogenic composition of the invention is in the form or a *B. bovis, B. bigemina, B. canis, B. caballi*, or *B. divergens* recombinant HAP2 protein or fragment thereof involved in evoking an immune response to *Babesia*. The immunogenic compositions/vaccines provided herein can be used to treat any mammal, including, but not limited to, cattle, equine, sheep, goats, pigs, bison, elk, camels, dogs, and deer.

In an embodiment, the invention is directed to a vaccine to prevent *Babesia* transmission by competent ticks, particularly in bison, deer, beef, equine, dogs, and cattle. The vaccine of the invention may be used for injectable, intranasal, or oral delivery to the recipient animal, and may be combined with other vaccine components such as *Pasteurella multocida, Histophilus somni*, and/or viral components such as Bovine herpes virus 1 (BHV-1), parainfluenza virus type 3 (PI3V), and bovine respiratory syncytial virus (BRSV). The other vaccine component may include genetically transformed *Babesia* parasites constitutively expressing a *B. bovis, B. bigemina, B. canis, B. caballi*, or *B. divergens* HAP2 antigen.

In an embodiment, the invention relates to immunogenic compositions/vaccines that can be used to control *Babesia* transmission by competent ticks. In an embodiment, the invention relates to methods of administering a vaccine/immunogenic composition as described herein. The methods involve administering an effective amount of a vaccine sufficient to prevent or lessen the extent of *Babesia* transmission by a competent tick in a subject, when the subject is later exposed to the tick.

In an embodiment, the invention is directed to a vaccine to control *Babesia* transmission by competent ticks. The vaccine may be to control transmission of *B. bovis, B. bigemina, B. canis, B. caballi*, or *B. divergens* by competent ticks. The vaccine/immunogenic composition may comprise at least one of an immunological adjuvant, a pharmaceutically acceptable carrier, a buffer, or a stabilizer.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Montana, USA), alum, mineral gels such as aluminum hydroxide gel, oil-in-water emulsions, water-in-oil emulsions such as, e.g., Freund's complete and incomplete adjuvants, Block copolymer (CytRx, Atlanta, Georgia, USA), QS-21 (Cambridge Biotech Inc., Cambridge Massachusetts, USA), SAF-M (Chiron, Emeryville California, USA), AMPHIGEN, proprietary oil in water adjuvant (Zoetis, Parsippany, New Jersey, USA), saponin, Quil A (Brenntag Biosector A/S, Ballerup, Denmark), or other saponin fraction, monophosphoryl lipid A, and Avridine lipid-amine adjuvant. Other immunomodulatory agents that can be included in the vaccine of the invention, comprise, e.g., one or more interleukins, interferons, or other known cytokines.

In some embodiments, at least one booster vaccine, is administered after the initial administration of the vaccine of the invention. The booster vaccine may be identical to the vaccine that is initially used to vaccinate the subject. The booster vaccine may be administered as early as four weeks after initial vaccination. In some embodiments, the booster vaccine may be administered at least one year after initial vaccination.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

An effective amount of any of the vaccines described herein can be determined by conventional means, starting with a low dose of the *B. bovis* antigen, and then increasing the dosage while monitoring the effects. An effective amount may be obtained after a single administration of a vaccine, or after multiple administrations of a vaccine. Known factors can be taken into consideration when determining an optimal dose per animal. These include the presence of other drugs in the animal, the species, size, age, and general condition of the animal, and the like.

One method of detecting whether an adequate immune response has been achieved is to determine seroconversion and antibody titer in the animal after vaccination. The timing of vaccination and the number of boosters, if any, will preferably be determined by a veterinarian based on analysis of all relevant factors, some of which are described above.

Suitable doses for vaccines according to the practice of the present invention range generally from about 50 µg to about 200 µg per dose, as may be determined by standard methods.

The effective dose amount of antigen of the present invention to be administered can be determined using known techniques, taking into account factors that can be determined by one of ordinary skill in the art such as the weight of the animal to be vaccinated. By way of example, vaccines may be delivered orally, parenterally, intradermally, subcutaneously, intramuscularly, intranasally or intravenously. Oral delivery may encompass, for example, adding the compositions to the feed or drink of the animals.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

The term "adjuvant", as used herein, means a pharmacological or immunological agent that modifies the effect of other agents, such as a drug or immunogenic composition. Adjuvants are often included in immunogenic compositions to enhance the recipient's immune response to a supplied antigen.

The terms "antibody" or "antibodies", as used herein, mean an immunoglobulin molecule able to bind to an antigen by means of recognition of an epitope. Immunoglobulins are serum proteins composed of "light" and "heavy" polypeptide chains, which have "constant" and "variable" regions, and are divided into classes (e.g., IgA, IgD, IgE, IgG, and IgM) based on the composition of the constant regions. An antibody that is "specific" for a given antigen indicates that the variable regions of the antibody recognize and bind a particular antigen exclusively. Antibodies can be a polyclonal mixture, or monoclonal. They can be intact immunoglobulins derived from natural or recombinant sources or can be immunoreactive portions of intact immunoglobulins. Antibodies can exist in a variety of forms, including Fv, Fab', F(ab')2, Fc, as well as single chain. An antibody can be converted to an antigen-binding protein, which includes, but is not limited to, antibody fragments. As used herein, the term "antigen binding protein", "antibody" and the like, which may be used interchangeably, refer to a polypeptide or polypeptides, or fragment(s) thereof, comprising an antigen binding site. The term "antigen binding protein" or "antibody" preferably refers to monoclonal antibodies and fragments thereof, and immunologic-binding equivalents thereof that can bind to a particular protein and fragments thereof. As used herein, the term encompasses not only intact polyclonal or monoclonal antibodies, but also fragments thereof. For the purposes of the present invention, "antibody" and "antigen binding protein" also includes antibody fragments, unless otherwise stated. Exemplary antibody fragments include Fab, Fab', F(ab')2, Fv, scFv, Fd, dAb, diabodies, their antigen-recognizing fragments, small modular immunopharmaceuticals (SMIPs) nanobodies and the like, all recognized by one of skill in the art to be an antigen binding protein or antibody fragment, and any of above-mentioned fragments and their chemically or genetically manipulated counterparts, as well as other antibody fragments and mutants thereof, fusion proteins comprising an antibody portion, and any other modified configuration of the immunoglobulin molecule that comprises an antigen recognition site. Antibodies and antigen binding proteins can be made, for example, via traditional hybridoma techniques (Kohler et al., Nature 256:495 499 (1975)), recombinant DNA methods (U.S. Pat. No. 4,816,567), or phage display techniques using antibody libraries (Clackson et al., Nature 352:624 628 (1991); Marks et al., J. Mol. Biol. 222:581 597 (1991)). For various other antibody production techniques, see Antibodies: A Laboratory Manual, eds. Harlow et al., Cold Spring Harbor Laboratory, 1988 as well as other techniques that are well known to those skilled in the art.

"Antigen", as used herein, means a molecule that contains one or more epitopes (linear, conformational or both), that upon exposure to a subject, will induce an immune response that is specific for that antigen. An epitope is the specific site of the antigen which binds to a T-cell receptor or specific B-cell antibody, and typically comprises about 3 to about 20 amino acid residues. The term "antigen" can also refer to subunit antigens—antigens separate and discrete from a whole organism with which the antigen is associated in nature—as well as killed, attenuated, or inactivated bacteria, viruses, fungi, parasites, or other microbes. The term "antigen" also refers to antibodies, such as anti-idiotype antibodies or fragments thereof, and to synthetic peptide mimotopes that can mimic an antigen or antigenic determinant (epitope). The term "antigen" also refers to an oligonucleotide or polynucleotide that expresses an antigen or antigenic determinant in vivo, such as in DNA immunization applications. An "antigen", as used herein, is a molecule or a portion of a molecule capable of being specifically bound by an antibody or antigen binding protein. In particular, an antibody, or antigen binding protein, will bind to epitopes of the antigen. An epitope, as used herein, refers to the antigenic determinant recognized by the hypervariable region, or Complementarity Determining Region (CDR), of the variable region of an antibody or antigen binding protein.

The term "animal", as used herein, means any animal that is susceptible to infection by *Babesia*, both domesticated and wild. Preferably, "animal", as used herein, refers to a bovine, a horse, or a dog.

The term "attenuated", as used herein, refers to a strain of a microorganism whose pathogenicity has been reduced so that it will generally initiate an immune response but without producing disease. An attenuated strain is less virulent than the parental strain from which it was derived. Attenuated microorganisms can be screened in vitro or in vivo to confirm that they are less pathogenic than its parental strain. Conventional means are used to introduce attenuating mutations, such as in vitro passaging, as well as chemical mutagenesis. An alternative means of attenuating comprises making pre-determined mutations using site-directed mutagenesis, where one or more mutations may be introduced. The term "more attenuated", as used herein, refers to a strain which has been further modified beyond the attenuated strain from which it was derived. This further attenuation can be achieved through additional in vitro passaging, or additional rounds of chemical or site-directed mutagenesis. To be useful as a live vaccine, any attenuated organism must nonetheless cause the host immune system to initiate an effective immune response, which may require some growth of the organism.

The term "bovine", as used herein, means a diverse group of medium- to large-sized ungulates, generally having cloven hoofs, and at least one of the sexes having true horns. Bovines include, but are not limited to, domestic cattle, bison, African buffalo, water buffalo, yak, and four-horned or spiral-horned antelope.

The term "pharmaceutically-acceptable carrier", as used herein, refers to substances which are, within the scope of sound medical judgment, suitable for use in contact with the tissues of animals, without undue toxicity, irritation, allergic response, and the like, commensurate with a reasonable benefit-to-risk ratio, and effective for their intended use.

The term "effective amount, "as used herein, means an amount of an active ingredient, e.g., an agent according to the invention, with or without an adjuvant, as appropriate under the circumstances, provided in a single or multiple doses as appropriate, sufficient to effect beneficial or desired results when administered to a subject or patient. An effective amount can be administered in one or more administrations, applications or dosages. A therapeutically effective amount of a composition according to the invention may be readily determined by one of ordinary skill in the art, and provides a measurable benefit to a patient, such as protecting the animal from subsequent challenge with a similar pathogen.

The terms "prevent", "preventing" or "prevention", and the like, as used herein, mean to inhibit the replication of a microorganism, to inhibit transmission of a microorganism, or to inhibit a microorganism from establishing itself in its host. These terms, and the like, can also mean to inhibit or block one or more signs or symptoms of infection.

As used herein, the term "affinity tag" relates to a polynucleotide encoding a peptide appended to a polynucleotide encoding HAP2 to assist in its purification.

As used herein, the term "about" is defined as plus or minus ten percent of a recited value. For example, about 1.0 g means 0.9 g to 1.1 g.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Preparation and Expression of rHAP2

The sequence of the hap2 gene was codon-optimized for expression in procaryotes, cloned into an expression vector, and the resulting rHAP2 protein expressed in bacteria.

Briefly, the *B. bovis* hap2 gene sequence was codon-optimized for expression in prokaryotic cells, chemically synthesized, and cloned into vector pET-30a(+) with a 6His tag for protein expression in bacterial cells. The codon-optimized HAP2 nucleotide sequence is CATA TGGTAATAATATCAAGTCTAAGGCAATGTATAAAC-AAGGGAACTGGGAAAGTTACC GAAAGCGAT-TGCCAGTGGCGTAGCCATACCAACGTGGACG-TTCGTGGTGGCGAGCT GAGCACCAGCTACGT-GCTGCGTAAGAAAGATAACCCGAACAGCGGT-CTGTATATCC ACATTCAGACCGCGATCACCACCC-TGACCTACAACCTGGTGTATCAATTCGACGCGC CGTACATGTATCGTGAGCACAACGGTGCGCTG-GAATACAGCCAGGTTGCGGGCATG TGCGA-CAGCTGCGATAAAATCGAGATTAAGAAATGC-ACCCTGCCGGAGGAAGTGCC GCCGAAGCT-GAAGGATAAGTTTGTTAACAAAACCTGCTG-CATCTGCGGCAAGAACG TGCCGAGCACCG-CGGTTCGTCAAAACCTGAAATGCAGCGGTTG-GAGCTTCGGCTTTC TGTACAGCAACTGCGT-GAGCCTGAGCTGCCTGGAAATCGTTGGCCCGT-GGTACAGCA TTTATAAGCCGCAGTACCCGCCGGA-CATCAACCGTCGTATTTTCGTGGATGTTTATA GCTTTGACGGTGATGCGGGCATCATTCCGGACGT-GAGCAAGAAAGGTTATCAAAAC AGCAAGCTG-CCGGACGAAACCCGTTACCTGAAGGAACCGGTT-TATAAAGATGGTCA CCTGAAGTTCACCATGAGCAC-CAACGCGGGCGCGGTGAAAAACGAAGACCTG- GATG TTAAGTTTACCATCATTAGCCAGCAAT-GGGTGGACGGCAACGCGCCGATCCGTATGG ATAAATACGTTGCGGTTCCGACCTGGCCGGACAGC-CACCCGGATGTTCAGGGTAGC AGC CTGCGTTTC-GAGTGCCAGCAAGCGGACCGTCCGTAT-GAATGCCGTAAGGGCCA AGATAACGAGTG-CCGTATGGAACGTTGCGCGCTGAACGTGCGTGTT-ATTGAACCGA GCGCGGTGGATGTTACCGGTG-CGACCTGCGATAAAATTGGCGTGAGCATGGGTACC TGGGGCGACGAGAAGCGTCTGTGCAACCAGCAC-GAAGGTACCTGCATCCAGAACCA ACTGGCGTG-GTACTTCAAAGAATTTAGCAGCACCATGCGTCT-GCCGAAGCTGTATGG TAGCCAACCGATGATCGCG-CACAAACGTATTAGCGGCAGCGTGCCGGAT-GAGAAGA AAACCGTTCCGCTGCCGGCGGACA-AAGAAGCGATGAAGGATGCGACCTTTAGCAGC AAGCCGGCGGCGGCGGTTGCGGCGAAAACCCC-GAAGGGTGGCGCGAAGAAAAAGA AACAGAA-ACTGGACAGCAGCGAGTGGGAACACAAGGATC-TGCTGCACAGCATCGC GTACAACGTGCGT-CACGCGGACACCAGCCGTATCGAGATTGACAGCT-TCGATGCGA CCATGACCCTGATCATTGCGGAAGC-GGTTGGTTTTAT, and is set forth in SEQ ID NO: 1.

*E. coli* BL21 STAR (DE3) cells were transformed with the expression plasmid encoding rHAP2. Following transformation, single cells were grown in LB medium containing ampicillin, and the clone that best expressed the rHAP2 protein was chosen for further study. The rHAP2 protein was obtained from inclusion bodies and purified by Ni-column with a 95% purification rate. Confirmation of the rHAP2 molecular weight and level of protein purity were determined by separating on an SDS-PAGE gel, and using Western blot analysis using a mouse anti-6His antibody. As seen in FIG. 1A, rHAP2 ran on the SDS-PAGE gel as a single band at approximately the expected molecular weight. Similarly, FIG. 1B shows that the mouse anti-6His antibody produced a single band on the Western Blot. Identity confirmation of rHAP2 protein was performed by LC-MS/MS, as per the third party company's protocol (GenScript USA; Piscataway, New Jersey, USA). The recombinant protein was stored at −80° C. until further use This example shows the production of a recombinant HAP2 protein of high purity in bacteria.

Example 2

Vaccination of Cattle with rHAP2

An experimental vaccine was formulated by mixing saponin adjuvant with the rHAP2 protein at a final concentration of 50 μg/ml. This preparation was used for vaccination of calves.

Two groups of three male Holstein calves aged 3 to 4 months were inoculated subcutaneously for four times at 21-day intervals (days 0, 21, 42, and 63). Group 1 (animals C1646, C1647 and C1649) was immunized with rHAP2 in adjuvant, and Group 2 (animals C1650, C1652 and C1653) received saponin adjuvant only (control). Serum samples were collected from each animal before and after inoculation, and analyzed by indirect ELISA (iELISA) for the presence of IgG against rHAP2.

Serological analysis using a rHAP2-iELISA demonstrated that all three calves vaccinated with rHAP2 in adjuvant developed antibody responses against rHAP2, while no reactivity was detected in sera from control calves inoculated with adjuvant alone. As seen in FIG. 2A and FIG. 2B, the levels of antibody response in vaccinated calves increased significantly on day 42 post-inoculation (PI), after the second boost inoculation with rHAP2. The anti-HAP2 antibody levels were maintained throughout the experiment until day 93 PI. The dotted line on FIG. 2B represents the cutoff value of the iELISA, calculated as the OD of non-infected cattle sera +3 SD.

Eight days after the fourth rHAP2 inoculation, one gram *R. microplus* larvae (La Minita strain) were applied under a cloth patch on all vaccinated and control calves (day 71 after the first inoculation). Thirteen days after infestation (day 84 post first inoculation), *R. microplus* nymphs began molting to adults, and calves were inoculated with approximately $10^7$ *B. bovis* S74-T3Bo Texas strain (virulent, tick-transmissible strain) infected red blood cells (RBC) using the IV route. Sera from experimental animals was collected before tick application, during acute *B. bovis* infection, and throughout the experiment to be used in further analyses. All six experimental calves were monitored daily for clinical signs of acute babesiosis, such as fever (higher than 38.8° C.), drop in packed cell volume (PCV), and parasite load in peripheral blood. The parasite load was measured by qPCR as described by R. G. Bastos et al. (2009, "Silencing of a putative immunophilin gene in the cattle tick *Rhipicephalus* (*Boophilus*) *microplus* increases the infection rate of *Babesia bovis* in larval progeny," Parasit. Vectors. 2(1):57. doi: 10.1186/1756-3305-2-57). During tick infestation and acute *B. bovis* infection, the animals were also monitored for the development of antibodies against rHAP2 by iELISA.

Figure 3A:
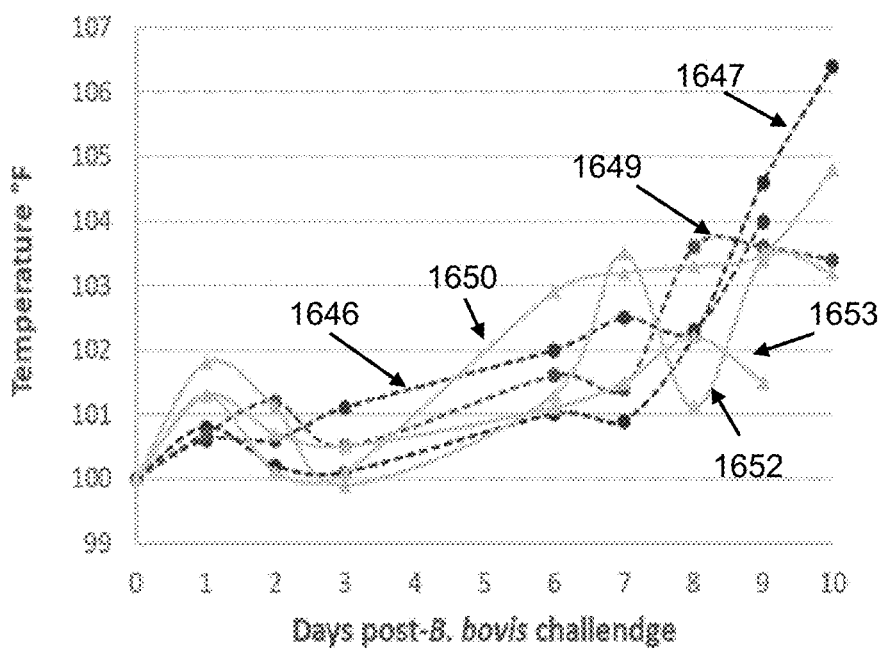
FIG. 3A to FIG. 3D depict graphs of the clinical parameters on acquisition feeding calves challenged with *B. bovis* S74-T3Bo.
Figure 3B:
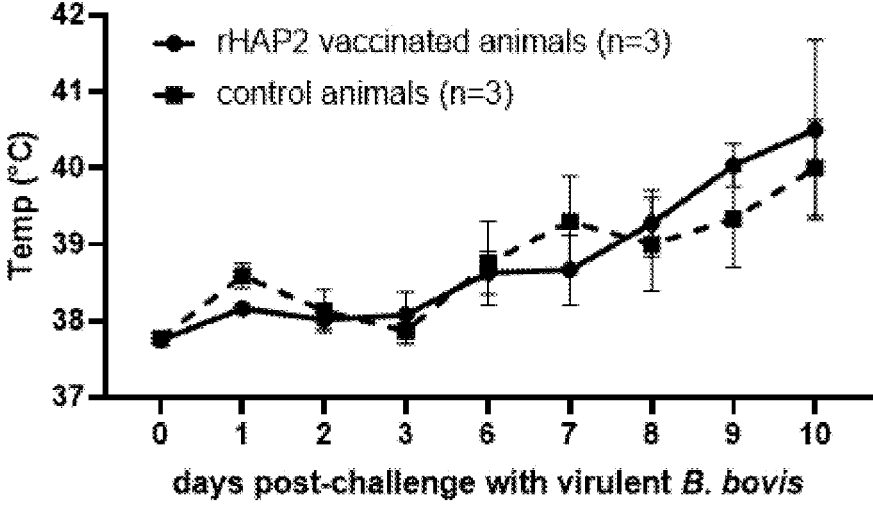
Figure 3C:
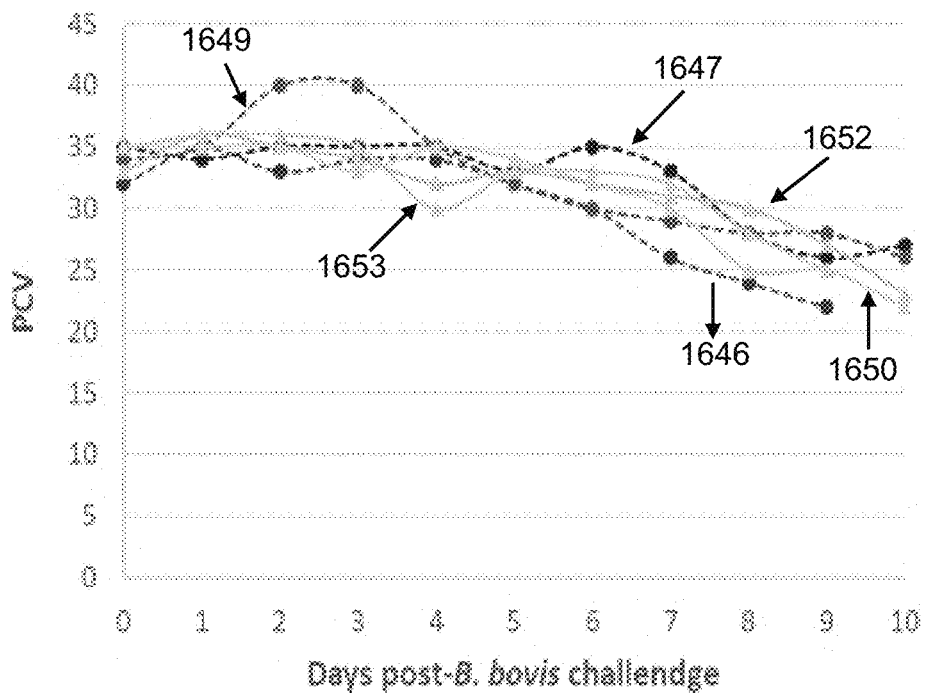
Figure 3D:
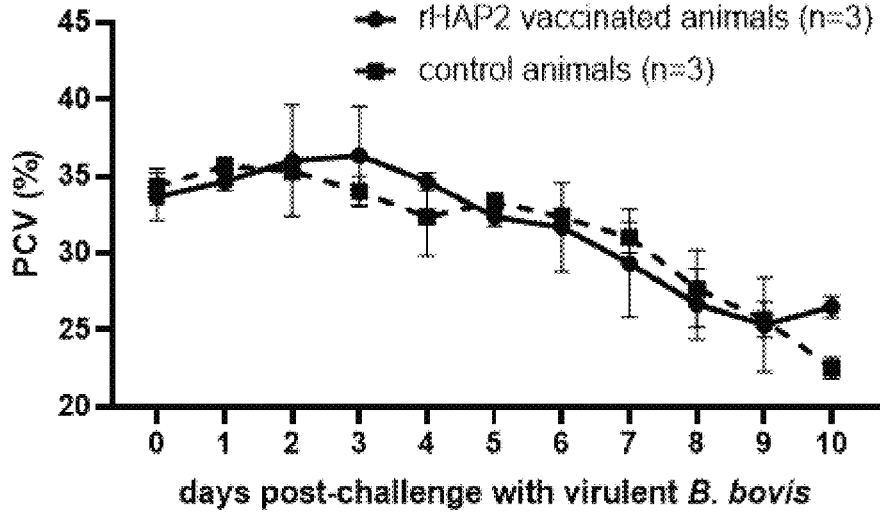

As can be seen in FIG. 3A and FIG. 3B, starting at 7 days post *B. bovis* S74-T3Bo infection, the mean rectal temperature increased in a similar fashion in both vaccinated and controls calves. In addition, as shown in FIG. 3C, packed cell volume (PCV) started decreasing 5 days after parasite challenge in all six experimentally-infected calves. The timing and intensity of alterations in temperature and PCV are clinical markers of acute babesiosis, and fully consistent with similar experiments involving acute infection of cattle with the *B. bovis* ST4-T3Bo Texas strain published by W. L. Goff et al. (1998, "*Babesia bovis* immunity. In vitro and in vivo evidence for IL-10 regulation of IFN-gamma and iNOS," Ann. N. Y. Acad. Sci. 849: 161-180. Overall, no significant differences were found among vaccinated and control groups regarding changes in body temperature and PCV during acute infection. Additionally, all experimentally infected calves, regardless of their vaccination status, showed other typical clinical signs of bovine babesiosis, such as loss of appetite and apathy.

The amounts of *B. bovis* parasite DNA circulating in peripheral blood were evaluated by quantitative PCR (qPCR) analyses performed in total DNA extracted from the animals at different times during the experimental infection. The single copy *B. bovis* msa-1 gene was used as target to detect *Babesia* DNA by qPCR.

Genomic DNA was analyzed by qPCR for the detection of the *B. bovis* msa-1 gene, and serum samples were analyzed for the detection of antibodies against the *B. bovis* HAP2 by iELISA. Briefly, iELISA for the detection of antibodies against HAP2 was performed by diluting the antigen in 0.05 M carbonate-bicarbonate buffer, pH 9.6, to a final concentration of 0.8 μg/ml. Fifty μl of the diluted antigen was added per well in a 96-well IMMULON 2HB Flat-Bottom MICROTITER ELISA plates (Thermo Fisher Scientific; Waltham, Massachusetts, USA) and incubated overnight at 4° C. After incubation, plates were washed 3 times with 200 μl per well of Washing/Blocking/Dilution buffer containing 0.2% I-BLOCK casein-based blocking reagent, in 1×PBS-T (Phosphate Buffered Saline (PBS) with 0.1% Tween 20 non-ionic detergent), and incubated with 300 μl per well of buffer for 1 hour at 30° C. Then, 50 μl of bovine serum diluted 1:400 in buffer was added per well, and plates incubated for 1 hour at 30° C. After five washes in PBS-T, 50 μl HRP-conjugated anti-bovine antibodies diluted 1:1, 100 in buffer was added per well. Plates were incubated for 45 minutes at 30° C. and washed 4 times with buffer, followed by 2 washes with PBS-T. Colorimetric detection was performed by adding 55 μl per well of 1-STEP ULTRA TMB-ELISA Substrate Solution (Thermo Fisher Scientific) for 10 minutes. The reaction was stopped by adding 55 μl per well of 2M $H_2SO_4$ solution, and the absorbance of each well was read at 450 nm using a spectrophotometer.

The iELISA for detection of antibodies against RAP-1/CT was performed by diluting rRAP-1/CT to a final concentration of 5 μg/ml, and diluting sera 1:50 in 0.2% I-BLOCK casein-based blocking reagent, in 1×PBS-T (Phosphate Buffered Saline (PBS) with 0.1% Tween 20 non-ionic detergent). The remaining protocol was performed as described above. Sera from calf C37816 was derived from an experimentally *B. bovis*-infected cattle. The mAb BABB75 used as a control in the iELISA was previously described by W. L. Goff et al. (1988, "Identification of *Babesia bovis* merozoite surface antigens by using immune bovine sera and monoclonal antibodies," Infect. Immun. 56(9): 2363-2368. doi: 10.1128/iai.56.9.2363-2368).

Real-time qPCR to detect *B. bovis* gDNA was performed as described by R. G. Bastos et al. (2009, supra). Briefly, gDNA was extracted from bovine peripheral blood using QIAMP DNA BLOOD Mini Kit (QIAGen) and 100 ng was used for amplification. Primers (GATGCGTTTGCA-CATGCTAAG, set forth in SEQ ID NO: 2, and CGGGTACTTCGGTGCTCTCA, set forth in SEQ ID NO: 3) and probe (CACGCTCAAGTAGGAAATTTTGT-TAAACCTGGA, set forth in SEQ ID NO: 4) specific for *B. bovis* msa-1 were used at 60° C. of annealing temperature. Reactions were performed in duplicates in 20 μl using 200 nM of primes and 100 nM of probe. Quantification of *B. bovis* msa-1 copies was calculated based on a plasmid standard curve. Efficiency of amplification was performed to evaluate analytical sensitivity of the qPCR and amplicons were sequenced to assess specificity of the reaction. The msa-1 amplification results are shown in FIG. 4A and FIG. 4B. In FIG. 4A the results are presented as copies of *B. bovis* msa-1 per 0.5 μg of gDNA, and in FIG. 4B the results are presented as copies of *B. bovis* msa-1 per 10 μl of blood. As seen in these figures, the levels of msa-1 gene DNA detected among the infected calves were highly variable among all the time points tested. However, no statistical differences were found in the qPCR data on days 0 (P=0.64), 3 (P=0.69,) 7 (P=0.81) and 9 (P=0.38) post challenge, among grouped rHAP2 vaccinated (C1646, C1647 and C1649) and control adjuvant inoculated (C1650, C1652 and C1653) calves.

Taken together, these data suggest that vaccination with rHAP2 elicited a strong antibody response against the HAP2 antigen but did not affect the natural clinical course of infection upon IV challenge with the *B. bovis* virulent strain S74-T3Bo. In addition, as seen in FIG. 2, no increment in the titer of anti-HAP2 antibodies was observed in sera from vaccinated calves on day 11 post-*B. bovis* infection, which is consistent with lack of expression of HAP2 in blood stages of the parasites.

Example 3

Analyses of Adult Ticks, Eggs, and *Larvae*

The majority of engorged *R. microplus* female ticks dropped after 9 days post-*B. bovis* infection in all experimental animals, also suggesting that vaccination with rHAP2 had no effect on the pattern of tick feeding, despite the ongoing acute parasite infection. All recovered engorged ticks were incubated in plates at 28° C. for egg collection. Eggs obtained from these ticks were used for further comparative analysis, and for transmission feeding experiments.

The number of replete female ticks recovered, the total egg masses, and the number of kinetes present in hemolymph in randomly selected replete ticks (72 per experimental animal) fed on vaccinated and control calves were evaluated.

Engorged female ticks were collected daily from days 6 to 10 of feeding, coinciding with the peak of *B. bovis* parasitemia. The total number of replete ticks recovered per animal is shown in the Table below, and in FIG. 5A and FIG. 5B.

| | Number of Engorged Female Ticks Days of feeding | | | | | |
|---|---|---|---|---|---|---|
| | Day 5 | Day 6 | Day 7 | Day 8 | Day 0 | Day 10 |
| C1646 (rHAP2 vac) | 46 | 611 | 475 | 99 | 12 | 0 |
| C1647 (rHAP2 vac) | 1 | 228 | 505 | 156 | 30 | 10 |
| C1649 (rHAP2 vac) | 8 | 599 | 738 | 142 | 14 | 1 |
| C1650 (control) | 16 | 446 | 458 | 71 | 14 | 20 |
| C1652 (control) | 12 | 531 | 430 | 113 | 30 | 7 |
| C1653 (control) | 6 | 206 | 338 | 66 | 11 | 0 |

Interestingly, the total number of replete female ticks recovered from vaccinated calves (about 3,600) was significantly larger than the total number of replete female ticks recovered from control animals (about 2,600). The total weight of ticks from the vaccinated animals was 207.9 grams, while total weight of ticks from the control animals was 184.4 grams (n=48). Despite this trend, no statistical difference was found between weights of the vaccinated and the control groups (P=0.06). Interestingly, the weight of eggs from ticks fed on vaccinated and control groups was statistically different (P=0.023). Total eggs weight over the 5 days was 57.9 grams on vaccinated animals and 49.4 grams on control animals (n=48). This suggests that infection of ticks with *B. bovis*, which presumably only occurred in the ticks that fed on animals from the non-HAP2 vaccinated group, might affect the reproductive fitness of the ticks.

Dropped, engorged female ticks were rinsed in tap water, placed into individual 24-well tissue culture plates, and incubated at 26° C. and 96% relative humidity. Eight days after collection, 72 replete female ticks per calf were evaluated for 5 days for the presence of kinetes in their hemolymph. A drop of hemolymph was placed on a glass slide, stained with DIFF QUIK diagnostic reagent, and observed under 100× amplification on an optical microscope. Kinetes were observed only in the hemolymph of two ticks 8 dpi, which were obtained from the control animals C1650 and C1652, respectively.

In addition, hemolymph from 18 individual replete female ticks per calf was also collected for genomic DNA (gDNA) extraction to detect the *B. bovis* rap-1 gene by nested PCR (nPCR), as described by C. E. Suarez et al. (2012, "Acute and persistent infection by a transfected Mol strain of *Babesia bovis*, (Mol. Biochem. Parasitol. 0.185(1):52-57.

doi: 10.1016/j.molbiopara.2012.05.003. Epub 2012 June 2.PMID: 22669120), and the results are presented in Table 2, below. This table presents the number of nPCR-positive samples for *B. bovis* (n=18 ticks).

TABLE 2

| | Number of nPCR-Positive Samples | | | | |
|---|---|---|---|---|---|
| | Days post-inoculation | | | | |
| | 6 | 7 | 8 | 9 | Total |
| C1646 | 2 | 1 | 2 | 0 | 5 |
| C1647 | 4 | 1 | 4 | 8 | 17 |
| C1649 | 4 | 4 | 0 | 8 | 16 |
| C1650 | 3 | 4 | 9 | 8 | 24 |
| C1652 | 2 | 0 | 5 | 8 | 15 |
| C1653 | 1 | 1 | 7 | 8 | 17 |
| Vaccinated grouped | | | | | 38 |
| Control grouped | | | | | 56 |

Example 4

*B. bovis Larvae* Transmission Studies

*Larvae* from female ticks fed on rHAP2-vaccinated and control calves were used for transmission experiments. *B. bovis* is acquired by adult *Rhipicephalus* ticks and transovarially-transmitted to offspring larvae, which then are implicated in transmitting the parasite to naïve cattle. Therefore, it was of interest to evaluate the ability of larvae from ticks fed on HAP2-vaccinated animals to transmit the parasite to naïve calves. To this end, the development of acute signs of *B. bovis* infection in two groups of three naïve calves that received either pooled *R. microplus* larvae from ticks collected from HAP2-vaccinated calves or larvae from ticks fed on control animals were evaluated. Clinical parameters were compared among all experimental calves.

Two groups of three male 3 to 4 months old Holstein calves were used as recipients for tick infestation. Approximately 1,000 larvae weighing about 0.25 grams were applied under cloth patches to every calf. A group of three calves (C99555, C99556, C99557) received a pool of larvae collected from animals previously vaccinated with rHAP2. Another group of three control recipient animals (C99562, C99561, C99559) were infested with larvae collected from control non-vaccinated animals that did not receive the rHAP2 antigen. All animals were checked daily for clinical signs of acute bovine babesiosis, such as fever higher than 38.8° C., a drop in PCV, and parasitemia by microscopy. Peripheral blood was collected for serology and gDNA extraction before and after tick infestation.

As seen in FIG. 6A and FIG. 6B, none of the calves infested with larvae from HAP2-vaccinated animals displayed detectable fever, and as seen in FIG. 6C and FIG. 6D, no significant decrease in PCV was detected in any of the rHAP3-vaccinated animals. In contrast, the three calves in the control group showed fever (higher than 38.8° C.), a significant drop in PCVs (30%), and typical clinical symptoms of acute babesiosis, such as prostration, anorexia, and increased respiratory lethargy. All experimental calves were also analyzed for the presence of parasite DNA by qPCR, and for the presence of immune humoral responses against *B. bovis* by iELISA. As seen in FIG. 7A and FIG. 7B, the presence of *B. bovis* DNA was detected in all control animals, but not in the three calves that received tick larvae from the HAP2-vaccinated animals. In addition, as seen in FIG. 8A and FIG. 8B, none of the three asymptomatic animals developed antibodies against *B. bovis* until the end of the experiment, 18 days after exposure to the ticks. The lack of antibodies in these three animals was also confirmed by Western blot analysis. Control calves were humanely euthanized at day 13 after larvae infestation due to the severity of acute babesiosis.

Collectively, these results demonstrated that vaccination with HAP2 abrogates the transmission of *B. bovis* by larvae of *R. microplus* ticks.

in SEQ ID NO: 1; the antigen being capable of blocking transmission of *Babesia* by competent ticks.

2. A cell expressing the antigen of claim 1.

3. A composition comprising the antigen of claim 1, wherein the composition is a host cell, a vaccine, or an immunogenic composition.

4. The composition of claim 3, wherein the composition is a vaccine and optionally comprises at least one of an immunological adjuvant, a pharmaceutically acceptable carrier, a buffer, or a stabilizer.

We claim:

1. A *Babesia* antigen comprising an about 80 kilodalton recombinant *Babesia* gametocyte HAPLESS2/GCS1 (HAP2) protein from *B. bovis*, and at least one affinity tag; wherein the recombinant HAP2 protein is encoded by a polynucleotide comprising the nucleotide sequence set forth

5. The composition of claim 4, wherein the vaccine further comprises at least one of an immunological adjuvant, a pharmaceutically acceptable carrier, a buffer, or a stabilizer.

6. A method for interfering with *Babesia* transmission by competent ticks, the method comprising administering to cattle an effective amount of the composition of claim 3, wherein the competent ticks that feed on vaccinated cattle do not transmit *Babesia*.

7. A method for interfering with *Babesia* transmission by competent ticks, the method comprising administering to cattle an effective amount of the composition of claim 4, wherein the competent ticks that feed on vaccinated cattle do not transmit *Babesia*.

8. A kit comprising the antigen of claim 1.

\* \* \* \* \*